United States Patent
Xie

(10) Patent No.: US 10,138,132 B2
(45) Date of Patent: Nov. 27, 2018

(54) SYNTHESIS OF MTW FRAMEWORK TYPE MOLECULAR SIEVES

(71) Applicant: Chevron U.S.A. Inc., San Ramon, CA (US)

(72) Inventor: Dan Xie, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/697,543

(22) Filed: Sep. 7, 2017

(65) Prior Publication Data

US 2018/0111836 A1    Apr. 26, 2018

Related U.S. Application Data

(60) Provisional application No. 62/411,788, filed on Oct. 24, 2016.

(51) Int. Cl.

| | |
|---|---|
| *C01B 39/42* | (2006.01) |
| *B01J 29/70* | (2006.01) |
| *C01B 39/48* | (2006.01) |
| *C01B 39/04* | (2006.01) |
| *C07D 211/14* | (2006.01) |
| *C01B 39/02* | (2006.01) |

(52) U.S. Cl.
CPC ............... *C01B 39/48* (2013.01); *B01J 29/70* (2013.01); *B01J 29/7034* (2013.01); *C01B 39/026* (2013.01); *C01B 39/04* (2013.01); *C01B 39/42* (2013.01); *C07D 211/14* (2013.01)

(58) Field of Classification Search
CPC ........ C01B 39/026; C01B 39/36–39/42; B01J 29/7034
See application file for complete search history.

(56) References Cited

U.S. PATENT DOCUMENTS

| | | | |
|---|---|---|---|
| 3,832,449 A | 8/1974 | Rosinski et al. | |
| 4,391,785 A | 7/1983 | Rosinski et al. | |
| 4,452,769 A | 6/1984 | Chu et al. | |
| 4,482,531 A | 11/1984 | Kuehl | |
| 4,537,758 A | 8/1985 | Chu et al. | |
| 4,539,193 A | 9/1985 | Valyocsik | |
| 4,552,738 A | 11/1985 | Rubin | |
| 4,552,739 A | 11/1985 | Kuhl | |
| 4,557,919 A | 12/1985 | Sumitani et al. | |
| 4,585,637 A | 4/1986 | Rubin | |
| 4,585,639 A * | 4/1986 | Szostak .................. | C01B 39/42 423/707 |

(Continued)

FOREIGN PATENT DOCUMENTS

| | | |
|---|---|---|
| CN | 1241986 A | 1/2000 |
| EP | 162719 | 11/1985 |

(Continued)

OTHER PUBLICATIONS

PCT International Search Report, International Patent Appl. No. PCT/US2017/050397, dated Dec. 8, 2017.

(Continued)

*Primary Examiner* — David M Brunsman
(74) *Attorney, Agent, or Firm* — Terrence M. Flaherty

(57) ABSTRACT

A method is disclosed for synthesizing MTW framework type molecular sieves using 1,1-diethyl-4-methylpiperidinium cations as a structure directing agent.

9 Claims, 2 Drawing Sheets

(56) References Cited

U.S. PATENT DOCUMENTS

| | | |
|---|---|---|
| 4,585,746 A | 4/1986 | Valyocsik |
| 4,622,214 A * | 11/1986 | Comyns ................ C01B 39/04 |
| | | 423/706 |
| 4,636,373 A | 1/1987 | Rubin |
| 4,743,437 A | 5/1988 | Whittam |
| 5,021,141 A | 6/1991 | Rubin |
| 5,137,705 A | 8/1992 | Valyocsik |
| 5,192,521 A | 3/1993 | Moini et al. |
| 6,652,832 B2 | 11/2003 | Malek |
| 8,202,506 B2 | 6/2012 | Lai et al. |
| 8,679,451 B2 | 3/2014 | Burton, Jr. et al. |
| 2008/0045767 A1 | 2/2008 | Cao et al. |
| 2011/0123433 A1* | 5/2011 | Burton ................ C01B 39/42 |
| | | 423/704 |
| 2011/0124940 A1* | 5/2011 | Burton, Jr. ........... B01J 29/7034 |
| | | 585/739 |
| 2015/0158020 A1* | 6/2015 | Nicholas ................ B01J 29/70 |
| | | 423/704 |

FOREIGN PATENT DOCUMENTS

| | | |
|---|---|---|
| GB | 2079735 | 1/1982 |
| WO | 2017180222 A1 | 10/2017 |

OTHER PUBLICATIONS

R. Bandyopadhyay, Y. Kubota, N. Sugimoto, Y. Fukushima and Y. Sugi "Synthesis of borosilicate zeolites by the dry gel conversion method and their characterization" Micropor. Mesopor. Mater. 1999, 32, 81-91.

\* cited by examiner

SYNTHESIS OF MTW FRAMEWORK TYPE MOLECULAR SIEVES

CROSS-REFERENCE TO RELATED APPLICATIONS

This application claims priority to U.S. Provisional Application Ser. No. 62/411,788, filed on Oct. 24, 2016, the disclosure of which is incorporated herein by reference.

TECHNICAL FIELD

The present disclosure is directed to the synthesis of MTW framework type molecular sieves.

BACKGROUND

Because of their unique sieving characteristics as well as their catalytic properties, crystalline molecular sieves and zeolites are especially useful in applications such as hydrocarbon conversion, gas drying and separation.

Molecular sieves identified by the International Zeolite Association as having the framework type MTW are known. Examples of MTW framework type materials include CZH-5, NU-13, Theta-3, TPZ-12, and ZSM-12. MTW framework type materials have a one-dimensional pore system with 12-membered rings.

U.K. Patent Application No. 2,079,735 discloses CZH-5 and its synthesis using choline as a structure directing agent.

U.S. Pat. No. 4,743,437 discloses NU-13 and its synthesis in the presence of a piperazine compound as a structure directing agent.

European Patent Application No. 162,719 discloses Theta-3 and its synthesis in the presence of a quaternary nitrogen compound of formula $BzNR_3^+X^-$ where Bz is a benzyl radical, R is hydrocarbyl group and $X^-$ is an anion.

U.S. Pat. No. 4,557,919 discloses TPZ-12 and its synthesis in the presence of a pyrrolidine- or piperidine-containing diammonium compound as a structure directing agent.

ZSM-12 and its conventional preparation in the presence of a tetramethylammonium or tetraethylammonium structure directing agent are disclosed in U.S. Pat. No. 3,832,449.

U.S. Pat. No. 4,391,785 discloses a method for the synthesis of ZSM-12 from a reaction mixture comprising, as a structure directing agent, a compound selected from the group consisting of a dimethylpyridinium halide and a dimethylpyrrolidinium halide.

U.S. Pat. Nos. 4,452,769 and 4,537,758 disclose methods for synthesizing ZSM-12 from a reaction mixture containing methyltriethylammonium cations as the structure directing agent.

Other structure directing agents that have been used to synthesize ZSM-12 include DABCO-$C_n$-diquat cations where n=4, 5, 6 or 10 (see U.S. Pat. No. 4,482,531), bis(dimethylpiperidinium)trimethylene cations (see U.S. Pat. No. 4,539,193), benzyltriethylammonium cations (see U.S. Pat. No. 4,552,738), dibenzyldimethylammonium cations (see U.S. Pat. No. 4,636,373), dimethyldiethylammonium cations (see U.S. Pat. No. 4,552,739), benzyltrimethylammonium cations (see U.S. Pat. No. 4,585,637), bis(N-methylpyridyl)ethylinium cations (see U.S. Pat. No. 4,585,746), hexamethyleneimine (U.S. Pat. No. 5,021,141), decamethonium cations (see U.S. Pat. No. 5,192,521), bis(methylpyrrolidinium) diquat-n ions where n=4, 5, or 6 (see U.S. Pat. No. 5,137,705), and 1,6-bis(2,3-dimethylimidazolium)hexane dications (see U.S. Pat. No. 8,679,451).

According to the present disclosure, MTW framework type molecular sieves have now been synthesized using 1,1-diethyl-4-methylpiperidinium cations as a structure directing agent, and, in some cases, it has been found that small crystal forms of the molecular sieve can be produced.

SUMMARY

In one aspect, there is provided a method of synthesizing a molecular sieve of MTW framework type, the method comprising: (a) preparing a reaction mixture comprising: (1) a source of silicon oxide; (2) a source of an oxide of a trivalent element; (3) a source of Group 1 or 2 metal; (4) a structure directing agent comprising 1,1-diethyl-4-methylpiperidinium cations; and (5) hydroxide ions; and (6) water; and (b) subjecting the reaction mixture to crystallization condition sufficient to form crystals of the molecular sieve.

In one aspect, there is provided a molecular sieve of MTW framework type comprising 1,1-diethyl-4-methylpiperidinium cations within its pore structure.

In its as-synthesized and anhydrous form, the MTW framework type molecular sieve has a chemical composition comprising, in terms of molar ratios, the following:

| $SiO_2/X_2O_3$ | 10 to 250 | 15 to 150 |
|---|---|---|
| $Q/SiO_2$ | >0 to 0.1 | >0 to 0.1 |
| $M/SiO_2$ | >0 to 0.1 | >0 to 0.1 | wherein X is a trivalent element, Q comprises 1,1-diethyl-4-methylpiperidinium cations and M is Group 1 or Group 2 metal.

DETAILED DESCRIPTION

Reaction Mixture

Figure 1:
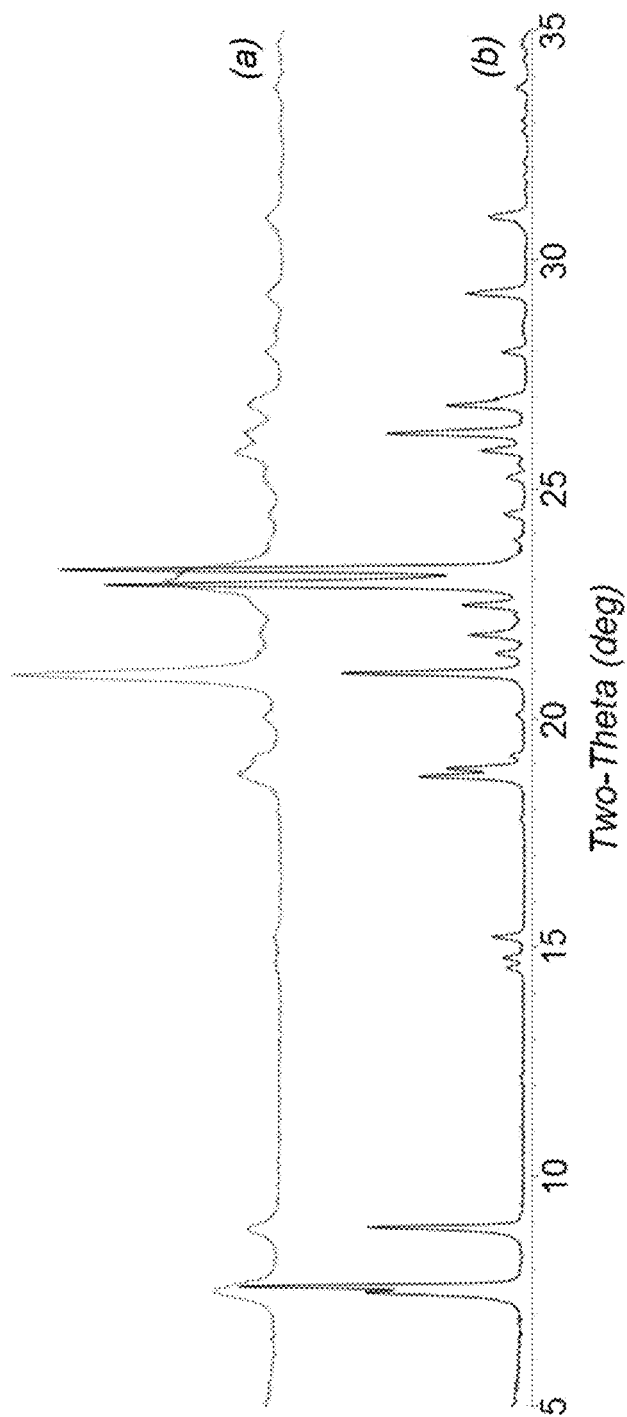
FIG. 1 compares the powder X-ray diffraction (XRD) patterns of (a) the as-synthesized borosilicate product of Example 1 and (b) a conventional MTW framework type molecular sieve.

In general, the MTW framework type molecular sieve is synthesized by: (a) preparing a reaction mixture comprising (1) a source of silicon oxide; (2) a source of an oxide of a trivalent element (X); (3) a source of a Group 1 or 2 metal (M); (4) a structure directing agent (Q) comprising 1,1-diethyl-4-methylpiperidinium cations; (5) hydroxide ions; and (6) water; and (b) subjecting the reaction mixture to crystallization conditions sufficient to form crystals of the molecular sieve.

The composition of the reaction mixture from which the molecular sieve is formed, in terms of molar ratios, is identified in Table 1 below:

TABLE 1

| Reactants | Useful | Exemplary |
|---|---|---|
| $SiO_2/X_2O_3$ | 10 to 250 | 15 to 150 |
| $M/SiO_2$ | 0.05 to 0.30 | 0.05 to 0.20 |
| $Q/SiO_2$ | 0.05 to 0.40 | 0.10 to 0.30 |
| $OH/SiO_2$ | 0.10 to 0.50 | 0.20 to 0.45 |
| $H_2O/SiO_2$ | 10 to 60 | 15 to 40 | wherein X is a trivalent element (e.g., one or more of boron and aluminum), Q comprises 1,1-diethyl-4-methylpiperidinium cations and M is Group 1 or Group 2 metal.

Suitable sources of silicon oxide include colloidal silica, fumed silica, precipitated silica, alkali metal silicates, and tetraalkyl orthosilicates.

Suitable sources of the trivalent element (X) can depend on the element X selected. Where X comprises or is boron, suitable sources of boron include boric acid and water-soluble borate salts (e.g., sodium borate). Where X comprises or is aluminum, suitable sources of aluminum include hydrated alumina and water-soluble aluminum salts (e.g., aluminum nitrate).

Combined sources of silicon and boron can additionally or alternatively be used and can include borosilicate zeolites (e.g., borosilicate beta zeolite).

Combined sources of silicon and aluminum can additionally or alternatively be used and can include aluminosilicate zeolites (e.g., zeolite Y) and clays or treated clays (e.g., metakaolin).

Examples of suitable Group 1 or Group 2 metals (M) include sodium, potassium and calcium, with sodium being preferred. The metal (M) is generally present in the reaction mixture as the hydroxide.

The structure directing agent (Q) comprises 1,1-diethyl-4-methylpiperidinium cations, represented by the following structure (1):

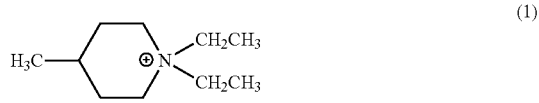

(1)

Suitable sources of Q are the hydroxides, chlorides, bromides, and/or other salts of the quaternary ammonium compound.

The reaction mixture may also contain seeds of a molecular sieve material, such as a MTW framework type molecular sieve, from a previous synthesis, desirably in an amount of from 0.01 to 10,000 ppm by weight (e.g., 100 to 5000 ppm by weight) of the reaction mixture.

For each embodiment described herein, the reaction mixture can be supplied by more than one source. Also, two or more reaction components can be provided by one source.

The reaction mixture can be prepared either batch wise or continuously. Crystal size, morphology and crystallization time of the crystalline molecular sieve described herein can vary with the nature of the reaction mixture and the crystallization conditions.

Crystallization and Post-Synthesis Treatment

Crystallization of the molecular sieve from the above reaction mixture can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 5 to 15 days. Crystallization is usually carried out in a closed system under autogenous pressure.

Once the molecular sieve crystals have formed, the solid product is recovered from the reaction mixture by standard mechanical separation techniques such as centrifugation or filtration. The crystals are water-washed and then dried to obtain the as-synthesized molecular sieve crystals. The drying step is typically performed at a temperature of less than 200° C.

As a result of the crystallization process, the recovered crystalline molecular sieve product contains within its pore structure at least a portion of the structure directing agent used in the synthesis.

The as-synthesized MTW framework type molecular sieve prepared as described herein may be subjected to subsequent treatment to remove part or all of the organic structure directing agent used in its synthesis. This can be conveniently effected by thermal treatment in which the as-synthesized material can be heated at a temperature of at least 370° C. for at least 1 minute and not longer than 24 hours. While sub-atmospheric and/or super-atmospheric pressures can be employed for the thermal treatment, atmospheric pressure may typically be desired for reasons of convenience. The thermal treatment can be performed at a temperature up to 925° C. Additionally or alternatively, the organic structure directing agent can be removed by treatment with ozone (see, e.g., A. N. Parikh et al., *Micropor. Mesopor. Mater.* 2004, 76, 17-22).

To the extent desired, the original Group 1 or Group 2 metal cations (e.g., $K^+$) of the as-synthesized molecular sieve can be replaced in accordance with techniques well known in the art by ion exchange with other cations. Preferred replacing cations include metal ions, hydrogen ions, hydrogen precursor (e.g., ammonium ions), and mixtures thereof. Particularly preferred replacing cations are those which tailor the catalytic activity for certain organic conversion reactions. These include hydrogen, rare earth metals and metals of Groups 2 to 15 of the Periodic Table of the Elements.

Where the molecular sieve formed is an intermediate molecular sieve, the target molecular sieve can be achieved using post-synthesis techniques such as heteroatom lattice substitution techniques and acid leaching techniques. For example, a small crystal form of an aluminosilicate MTW framework type molecular sieve (Al-MTW) can be prepared from a small crystal form of the borosilicate MTW framework type molecular sieve (B-MTW) by post-synthetic replacement of the boron in the borosilicate framework with aluminum. Replacement of boron in the borosilicate MTW framework type molecular sieve can be readily achieved by suitable treatment with an aluminum salt (e.g., aluminum nitrate) such as described in U.S. Pat. Nos. 6,468,501 and 6,790,433. At least 10% (e.g., at least 25%, or at least 50%) of the boron in borosilicate framework may be replaced with aluminum.

While not wishing to be bound by any theory, it is believed that Al re-insertion from B-MTW (i.e., indirect synthesis of Al-MTW) may allow for more localized replacement of B atoms (e.g., those in the 12-membered ring openings) by Al atoms in the structure. In contrast, it is believed that direct synthesis of Al-MTW results in Al being distributed more randomly distributed throughout the structure. S. I. Zones et al. (*J. Am. Chem. Soc.* 2014, 136, 1462-1471) reported that catalytic behavior can be changed dramatically due to the change of Al atomic positions (acid sites).

The present MTW framework type molecular sieve can be used as a sorbent. Alternatively or additionally, and particularly in its aluminosilicate form, the present MTW framework type molecular sieve can be used as a catalyst to facilitate one or more organic compound (e.g., hydrocarbon) conversion processes including many of present commercial/industrial importance. In particular, when combined with a hydrogenation component (e.g., Pt, Pd or Re), the present MTW framework type molecular sieve may be useful in the catalytic conversion of $C_{9+}$ alkylaromatic hydrocarbons, either alone or in the presence of toluene and/or benzene, to produce xylenes.

The present MTW framework type molecular sieve can be formulated into a catalyst composition by combination with other materials, such as binders and/or matrix materials, which provide additional hardness or catalytic activity to the finished catalyst.

Materials which can be blended with the present MTW framework type molecular sieve can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of the present MTW framework type molecular sieve contained in the final catalyst product can range from 1 to 90 wt. % (e.g., 2 to 80 wt. %) of the total catalyst.

Characterization of the Molecular Sieve

In its as-synthesized and anhydrous form, the present MTW framework type molecular sieve has a chemical composition, in terms of molar ratios, as shown in Table 2:

TABLE 2

|  | Broad | Exemplary |
|---|---|---|
| $SiO_2/X_2O_3$ | 10 to 250 | 15 to 150 |
| $Q/SiO_2$ | >0 to 0.1 | >0 to 0.1 |
| $M/SiO_2$ | >0 to 0.1 | >0 to 0.1 | wherein X is a trivalent element (e.g., one or more of boron and aluminum), Q comprises 1,1-diethyl-4-methylpiperidinium cations, and M is Group 1 or Group 2 metal. The term "as-synthesized" is employed herein to refer to the molecular sieve in its form after crystallization, prior to removal of the structure directing agent. The term "anhydrous form" is employed herein to refer to a molecular sieve substantially devoid of both physically adsorbed and chemically adsorbed water.

In its calcined from, the present MTW framework type molecular sieve has a chemical composition comprising the following molar relationship:

$$X_2O_3:(n)SiO_2$$

wherein X is a trivalent element and n has a value of 10 to 250 (e.g., 10 to 150, 15 to 250, 15 to 150, 20 to 250, or 20 to 150).

The MTW framework type molecular sieve prepared as described herein can form agglomerates of small crystals that may have crystallites sizes in a range of 10 to 250 nm (e.g., 25 to 200 nm, or 40 to 150 nm). These small crystals can be desirable for they generally lead to greater activity. Smaller crystals can mean greater surface area, which can lead to a greater number of active catalytic sites per given amount of catalyst. As used herein, the term "crystallite size" refers to the longest dimension of the crystal. Crystallite size can be determined by SEM analysis.

The present MTW framework type molecular sieve is characterized by X-ray diffraction. Powder X-ray diffraction patterns representative of MTW framework type molecular sieves can be referenced in the "*Collection of Simulated XRD Powder Patterns for Zeolites,*" Fifth Revised Edition, 2007 of the International Zeolite Association. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can result from variations in the organic compound used in the preparation. Calcination can also cause minor shifts in the X-ray diffraction pattern.

The powder X-ray diffraction patterns presented herein were collected by standard techniques. The radiation was $CuK_\alpha$ radiation. The peak heights and the positions, as a function of $2\theta$ where $\theta$ is the Bragg angle, were read from the relative intensities of the peaks, and d, the interplanar spacing corresponding to the recorded lines, can be calculated.

EXAMPLES

The following illustrative examples are intended to be non-limiting.

Example 1

12.10 g of deionized water, 0.42 g of a 45% KOH solution, 3.55 g of a 24.39% 1,1-diethyl-4-methylpiperidinium hydroxide solution, 0.103 g of boric acid and 5.00 g of LUDOX® AS-40 colloidal silica were mixed together in a Teflon liner. The gel was stirred until it became homogeneous. The liner was then capped and placed within a Parr Steel autoclave reactor. The autoclave was then put in an oven heated at 170° C. for 9 days. The solid products were recovered from the cooled reactor by centrifugation, washed with deionized water and dried at 95° C.

FIG. 1 compares the powder X-ray diffraction patterns of the as-synthesized borosilicate product of Example 1 in FIG. 1(a) and a conventional MTW framework type molecular sieve in FIG. 1(b). As depicted in FIG. 1, the powder XRD pattern of the as-synthesized product showed the typical phase of MTW topology and also indicated decreased crystal size as inferred from the peak broadening in the XRD pattern.

Figure 2:
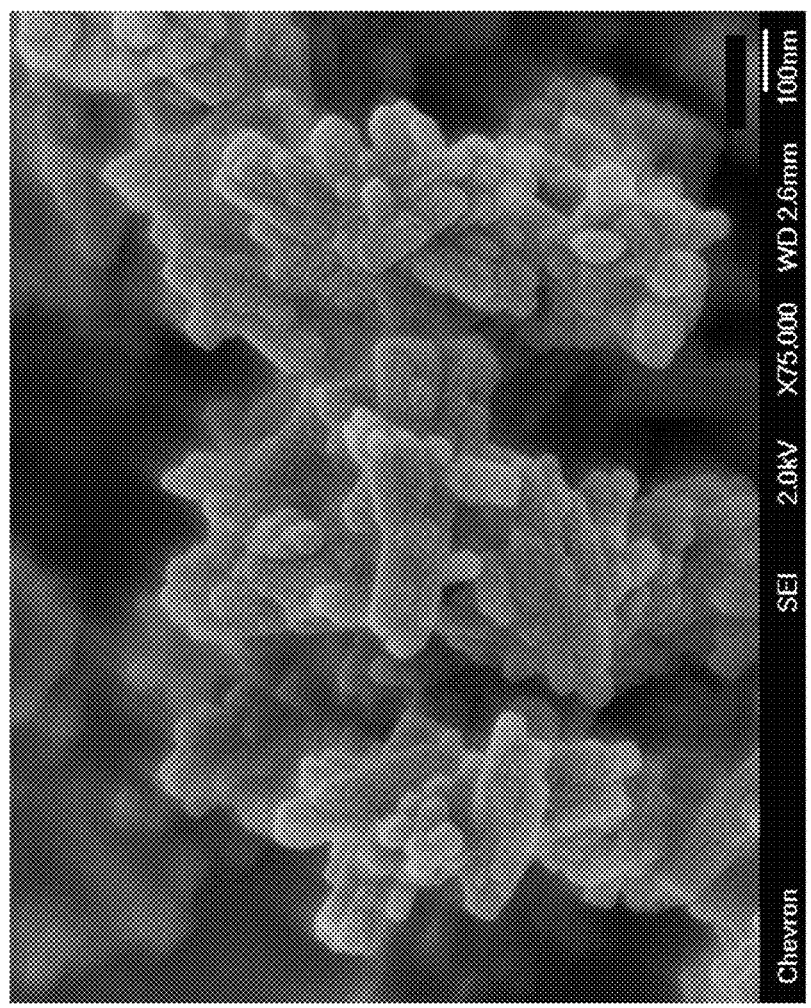
FIG. 2 is a Scanning Electron Micrograph (SEM) image of the as-synthesized product of Example 1.

FIG. 2 is a SEM image of the as-synthesized product and showed that the material was composed of agglomerates of plate-like crystals with an average length of about 100 nm and average width of about 60 nm.

The product had a $SiO_2/B_2O_3$ molar ratio of 38.7, as determined by ICP elemental analysis.

Example 2

4.84 g of deionized water, 0.17 g of a 45% KOH solution, 1.42 g of a 24.39% 1,1-diethyl-4-methylpiperidinium hydroxide solution, 0.017 g of boric acid and 2.00 g of LUDOX® AS-40 colloidal silica were mixed together in a Teflon liner. The resulting gel was stirred until it became homogeneous. The liner was then capped and placed within a Parr Steel autoclave reactor. The autoclave was then put in an oven heated at 170° C. for 7 days. The solid products were recovered from the cooled reactor by centrifugation, washed with deionized water and dried at 95° C.

The resulting product was identified by powder XRD and SEM as a pure borosilicate MTW-type molecular sieve. The crystal sizes of the product were about the same as the product of Example 1.

The product had a SiO$_2$/B$_2$O$_3$ molar ratio of 82.3, as determined by ICP elemental analysis.

Example 3

7.26 g of deionized water, 0.25 g of a 45% KOH solution, 2.13 g of a 24.39% 1,1-diethyl-4-methylpiperidinium hydroxide solution, 0.012 g of boric acid and 3.00 g of LUDOX® AS-40 colloidal silica were mixed together in a Teflon liner. The resulting gel was stirred until it became homogeneous. The liner was then capped and placed within a Parr Steel autoclave reactor. The autoclave was then put in an oven heated at 170° C. for 7 days. The solid products were recovered from the cooled reactor by centrifugation, washed with deionized water and dried at 95° C.

The resulting product was identified by powder XRD and SEM as a pure borosilicate MTW-type molecular sieve. The crystal sizes of the product were about the same as the product of Example 1.

The product had a SiO$_2$/B$_2$O$_3$ molar ratio of 114.6, as determined by ICP elemental analysis.

Example 4

26.68 g of deionized water, 1.00 g of a 45% KOH solution, 18.39 g of a 11.38% 1,1-diethyl-4-methylpiperidinium hydroxide solution and 5.00 g of CBV760 Y-zeolite powder (Zeolyst International, SiO$_2$/Al$_2$O$_3$ mole ratio=60) were mixed together in a Teflon liner. The resulting gel was stirred until it became homogeneous. The liner was then capped and placed within a Parr Steel autoclave reactor. The autoclave was then put in an oven heated at 160° C. for 6 days. The solid products were recovered from the cooled reactor by centrifugation, washed with deionized water and dried at 95° C.

The resulting product was identified by powder XRD and SEM as a pure aluminosilicate MTW-type molecular sieve. The crystal sizes of the product are about the same as the product of Example 1.

The product had a SiO$_2$/Al$_2$O$_3$ molar ratio of 29.2, as determined by ICP elemental analysis.

Example 5

The as-synthesized molecular sieve product of Example 1 was calcined inside a muffle furnace under a flow of air heated to 595° C. at a rate of 1° C./minute and held at 595° C. for 5 hours, cooled and then analyzed by powder XRD. The powder XRD data indicated that the material remains stable after calcination to remove the structure directing agent.

1.5 g of calcined molecular sieve was then added to 32 mL of a 1M solution of aluminum nitrate in a Teflon liner. The liner was capped and placed within a Parr Steel autoclave reactor. The autoclave was then put in an oven heated at 160° C. for 15 hours. The solid products were recovered from the cooled reactor by filtration, washed with deionized water.

The dry product was identified by powder XRD as a pure MTW-type molecular sieve. The powder XRD data showed that the diffraction peaks were shifted to lower angles compared to the XRD data collected from the initial calcined sample, these shifts are consistent with expansion of the molecular sieve lattice when aluminum is inserted into the framework.

The invention claimed is:

1. A method of synthesizing a molecular sieve of MTW framework type, the method comprising:
    (a) preparing a reaction mixture comprising:
        (1) a source of silicon oxide;
        (2) a source of an oxide of a trivalent element (X);
        (3) a source of Group 1 or 2 metal (M);
        (4) a structure directing agent (Q) comprising 1,1-diethyl-4-methylpiperidinium cations;
        (5) hydroxide ions; and
        (6) water; and
    (b) subjecting the reaction mixture to crystallization condition sufficient to form crystals of the molecular sieve.

2. The method of claim 1, wherein the reaction mixture has a composition, in terms of molar ratios, as follows:

| | |
|---|---|
| SiO$_2$/X$_2$O$_3$ | 10 to 250 |
| M/SiO$_2$ | 0.05 to 0.30 |
| Q/SiO$_2$ | 0.05 to 0.40 |
| OH/SiO$_2$ | 0.10 to 0.50 |
| H$_2$O/SiO$_2$ | 10 to 60. |

3. The method of claim 1, wherein the reaction mixture has a composition, in terms of molar ratios, as follows:

| | |
|---|---|
| SiO$_2$/X$_2$O$_3$ | 15 to 150 |
| M/SiO$_2$ | 0.05 to 0.20 |
| Q/SiO$_2$ | 0.10 to 0.30 |
| OH/SiO$_2$ | 0.20 to 0.45 |
| H$_2$O/SiO$_2$ | 15 to 40. |

4. The method of claim 1, wherein X comprises one or more of boron and aluminum.

5. The method of claim 1, wherein the crystallization conditions include a temperature of from 125° C. to 200° C.

6. A molecular sieve of MTW framework type comprising 1,1-diethyl-4-piperidinium cations within its pore structure.

7. The molecular sieve of claim 6, and having a composition, in terms of molar ratios, as follows:

| | |
|---|---|
| SiO$_2$/X$_2$O$_3$ | 10 to 250 |
| M/SiO$_2$ | >0 to 0.1 |
| Q/SiO$_2$ | >0 to 0.1 | wherein X is a trivalent element, Q comprises 1,1-diethyl-4-methylpiperidinium cations, and M is Group 1 or Group 2 metal.

8. The molecular sieve of claim 6, and having a composition, in terms of molar ratios, as follows:

| | |
|---|---|
| SiO$_2$/X$_2$O$_3$ | 15 to 150 |
| M/SiO$_2$ | >0 to 0.1 |
| Q/SiO$_2$ | >0 to 0.1 | wherein X is a trivalent element, Q comprises 1,1-diethyl-4-methylpiperidinium cations, and M is Group 1 or Group 2 metal.

9. The molecular sieve of any one of claim 7 or 8, wherein X comprises one or more of boron and aluminum.

* * * * *